United States Patent
John

(10) Patent No.: US 9,687,168 B2
(45) Date of Patent: Jun. 27, 2017

(54) NON-INVASIVE DEEP MUSCLE ELECTROMYOGRAPHY

(75) Inventor: Lester Ryan John, Gardens (ZA)

(73) Assignees: University of Cape Town (ZA); South African Medical Research Council (ZA)

(*) Notice: Subject to any disclaimer, the term of this patent is extended or adjusted under 35 U.S.C. 154(b) by 0 days.

(21) Appl. No.: 13/387,897

(22) PCT Filed: Jul. 29, 2010

(86) PCT No.: PCT/IB2010/001876
§ 371 (c)(1),
(2), (4) Date: Apr. 10, 2012

(87) PCT Pub. No.: WO2011/012988
PCT Pub. Date: Feb. 3, 2011

(65) Prior Publication Data
US 2012/0184838 A1    Jul. 19, 2012

(30) Foreign Application Priority Data
Jul. 30, 2009  (ZA) .................................. 2009/05309

(51) Int. Cl.
*A61B 5/04* (2006.01)
*A61B 5/0492* (2006.01)
(Continued)

(52) U.S. Cl.
CPC ........ *A61B 5/0492* (2013.01); *A61B 5/04012* (2013.01); *A61B 5/4519* (2013.01);
(Continued)

(58) Field of Classification Search
CPC ... A61B 5/0488; A61B 5/1107; A61B 5/4519; A61B 5/6802; A61B 5/6831; A61B 5/7264; G06K 9/0057
(Continued)

(56) References Cited

U.S. PATENT DOCUMENTS 5,513,651 A * 5/1996 Cusimano ............ A61B 5/0488
600/595
6,185,451 B1 * 2/2001 Richardson .......... A61B 5/0488
600/546
(Continued)

OTHER PUBLICATIONS

"Spine Anatomy", OrthopaedicsOne Articles. In: OrthopaedicsOne—The Orthopaedic Knowledge Network. http://www.orthopaedicsone.com/display/Main/Spine+anatomy.*
(Continued)

*Primary Examiner* — Devin Henson
(74) *Attorney, Agent, or Firm* — Andrus Intellectual Property Law LLP

(57) ABSTRACT

A method and apparatus for conducting electromyography of a deep muscle non-invasively are provided. An array of suitable surface electromyography electrodes is arranged in one or more rings encircling a part of the human body in which a deep muscle being investigated is located. The potential of at least selected electrodes relative to another electrode selected from a common reference electrode (mono-polar) and other electrodes (bi-polar) in the array is recorded and the data is processed in respect of the recorded potentials of at least some of said selected electrodes in order to determine (optionally using approximations or algorithms, or both) the contribution being made by at least the deep muscle being investigated. Typically, this is done mathematically by resolving the electromyography signals into their constituent components using a suitable technique. Preferably, this is integrated with a static muscle imaging device that may use the same electrodes to obtain a static tomogram of the muscles encircled.

7 Claims, 5 Drawing Sheets

(51) Int. Cl.
- *A61B 5/11* (2006.01)
- *G06K 9/00* (2006.01)
- *A61B 5/00* (2006.01)
- *A61B 5/0488* (2006.01)
- *A61B 5/053* (2006.01)
- *G06K 9/62* (2006.01)

(52) U.S. Cl.
CPC .......... *A61B 5/7203* (2013.01); *A61B 5/0488* (2013.01); *A61B 5/0536* (2013.01); *A61B 5/1107* (2013.01); *A61B 5/6802* (2013.01); *A61B 5/6824* (2013.01); *A61B 5/6831* (2013.01); *A61B 5/7264* (2013.01); *A61B 2562/0209* (2013.01); *A61B 2562/043* (2013.01); *G06K 9/0057* (2013.01); *G06K 9/624* (2013.01)

(58) Field of Classification Search
USPC .............................. 600/372, 382, 386, 393
See application file for complete search history.

(56) References Cited

U.S. PATENT DOCUMENTS

| | | | |
|---|---|---|---|
| 6,440,067 B1* | 8/2002 | DeLuca et al. | 600/300 |
| 6,720,984 B1* | 4/2004 | Jorgensen et al. | 715/863 |
| 7,254,500 B2* | 8/2007 | Makeig | A61B 5/048 324/76.19 |
| 7,409,242 B2* | 8/2008 | Maekawa et al. | 600/546 |
| 7,831,302 B2* | 11/2010 | Thomas | 600/546 |
| 8,447,704 B2* | 5/2013 | Tan | G06F 3/015 706/12 |
| 2006/0189882 A1 | 8/2006 | Thomas | |

OTHER PUBLICATIONS

Cappellini et al., "Motor Patterns in Human Walking and Running", J Neurophysiol, vol. 95, Issue 6, Jun. 2006, pp. 3426-37.*

Krouchev et al., "Sequential Activation of Muscle Synergies During Locomotion in the Intact Cat as Revealed by Cluster Analysis and Direct Decomposition", J Neurophysiol, vol. 96, Issue 5, Oct. 2006, pp. 1991-2010.*

Nakamura et al., "The application of independent component analysis to the multi-channel surface electromyographic signals for separation of motor unit action potential trains: part I—measuring techniques", Journal of Electromyography and Kinesiology, vol. 14, Issue 4, Aug. 2004, pp. 423-432.*

Kleine et al. "Influence of motoneuron firing synchronization on SEMG characteristics in dependence of electrode position", Journal of Applied Physiology, vol. 91, No. 4, Oct. 2001, pp. 1588-1599.*

McKeown M J et al, "Non-invasive monitoring of functionally distinct muscle activations during swallowing", Clinical Neurophysiology 2002 vol. 113 pp. 354-366.

McGill S et al, "Appropriately placed surface EMG electrodes reflect deep muscle activity (PSOAS, quadratus lumborum, abdominal wall) in the lumbar spine", Journal of Biomechanics 1996 vol. 29(11), pp. 1503-1507.

Azzerboni B et al, "A New Approach to Detection of Muscle Activiation by Independent Component Analysis and Wavelet Transform", Lecture Notes in Computer Science 2002 vol. 2486 pp. 109-116.

Biedermann F et al, "Surface EMG-recordings using a miniaturised matrix electrode: a new technique for small animals", Journal of Neuroscience Methods, 2000, vol. 97, pp. 69-75.

Semple R et al, "Tibialis posterior in health and disease: a review of structure and function with specific reference to electromyographic studies", Journal of Foot and Ankle Research, Aug. 19, 2009.

Murley G S et al, "Tibialis posterior EMG activity during barefoot walking in people with neutral foot posture," Journal of Electromyography and Kinesiology, 2009, vol. 19, pp. e69-e77.

McKeown M J et al, "A Combined Independent Component Analysis (ICA)/ Empirical Mode Decomposition (EMD) Method to Infer Corticomuscular Coupling", Proceedings of the 2nd International IEEE EMBS, Conference on Neural Engineering, Arlington, Virginia, Mar. 16-19, 2005, pp. 679-682.

US Neurological Diagnostic/Monitoring Equipment Market, #7565-56, 2000, Frost & Sullivan.

International Search Report dated Oct. 29, 2010.

Golding JSR, Electromyography of the Erector Spinae in low Back Pain, 1952, Postgrad Med J, 28: 401-402.

* cited by examiner

NON-INVASIVE DEEP MUSCLE ELECTROMYOGRAPHY

CROSS-REFERENCE TO RELATED APPLICATIONS

This application claims priority to PCT/IB2010/001876, filed Jul. 29, 2010, and published in English language as Publication No. WO 2011/012988 on Jul. 29, 2010, which claims priority to ZA Application No. 2009/05309, filed Jul. 30, 2009, incorporated herein by reference.

FIELD OF THE INVENTION

This invention relates to non-invasive deep muscle electromyography (EMG) to be used for recording the electrical activity of muscles in order to assess muscle function in a variety of different fields including sports, biomechanics research, physiotherapy and clinical neuro-muscular diagnostics.

BACKGROUND TO THE INVENTION

There are presently two categories of electromyography recordings. The first is a non-invasive surface electromyography (sEMG) in which adhesive bio-electrodes are placed on the surface of the skin directly above the muscle under investigation. This category is accordingly limited in application to superficial muscles that are close to the skin's surface.

The second category is an invasive procedure for obtaining electromyography recordings that utilises fine-wires or needles that physically pierce the skin in order to communicate with a so-called deep muscle that is under investigation. Not only is this technique invasive, but some deep muscles that are located close to major blood vessels, nerves, and viscera should not be investigated at all by such a technique for patient safety reasons. Such established invasive EMG techniques are described in a scientific review article by Jasper R Daube and Devon I Rubin (2009) entitled "Needle electromyography" in Muscle & Nerve 39, no. 2: 244-270.

Invasive electromyography carries with it a number of risks such as the potential for infliction of additional trauma on a patient as well as that of infection. Such risks thus preclude its routine use in sports performance testing and training, particularly for elite athletes who may risk a performance-reducing or livelihood-destroying injury or infection as a result of such a procedure.

There have been previous attempts to investigate deep muscles non-invasively. In international patent publication number WO 2004107976 there is described a method and device for assessing the function of a deep muscle of a subject in which a patient table, force transducers and an ultrasound device are employed for visualising the deep muscle of interest. A computer may be connected to the transducers and ultrasound device to provide cues to the subject during the conduct of an assessment session and to analyse information obtained from the session. The device may also include one or more slings for supporting a limb of the subject.

In U.S. Pat. No. 6,185,451 there is described a method and apparatus for assessing the function of deep joint stabilizing muscles in which superficial muscles are monitored using electromyography during performance of an activity known to require recruitment, primarily, of deep stabilizing muscles when performed correctly. If the deep muscle functions adequately, there is little activity of the superficial muscles. Conversely, if the deep muscle function is inadequate, the superficial muscle activity is increased. Monitoring of the superficial muscles using electromyography may be combined with monitoring of the deep joint stabilizing muscle using ultrasound imaging and/or pressure biofeedback. The apparatus includes a surface electromyography unit, an ultrasound unit, a pressure biofeedback unit and vitalograph, in combination with a computer programmed to analyze data from them and given an indication of function.

The sEMG of five specific deep muscles may be recorded on the surface using conventional sEMG methods, with a 15-20% error, as demonstrated by McGill et al (1996, J. Biomechanics, 29(11), p 1503-1507) who recorded psoas, quadratus lumborum, external & internal obliques and transversus abdominus muscles. However this is only applicable to those specific muscles and not generalizable to all deep muscles.

Jesinger & Stonic (1994, IEEE DSP Workshop Proc., p 57-60) proposed an inverse finite element modeling (FEM) method to resolve superficial from deep muscle activity. However this method requires a priori information such as a multiple-slice MRI image of the body segment. Such inverse FEM models do not provide unique mathematical solutions unless there are a large number (>>100) of measurement points, and despite being introduced in 1996, to date there is no clinical evidence that this method is practically able to resolve deep from superficial muscle activity. Using the same approach, now termed 'computed myography', but with a number of mathematical approximations, van den Doel et al (2008, Inverse Problems, 24, p 1-17) attempted to resolve biceps, brachialis, and triceps activity but was only successful in demonstrating biceps and triceps activity resolution since their posited brachialis component behaved identically to biceps. Triceps and biceps are however both antagonistic superficial muscles that are easily recorded and differentiated using standard sEMG anyway. This inverse FEM method therefore appears to be more suited to academic computer simulated experiments as opposed to a being a viable clinical investigation tool.

In summary, as far as applicants are aware, aside from five specific deep muscles (McGill et al, 1996), deep muscle activity may currently only be actually recorded using the already established invasive electromyography techniques, and the two hypothesised techniques suggested by the non-invasive patents involving relating deep muscle activity to ultrasound imaging of changes in width and indirect inference of deep muscle activity by monitoring co-agonist superficial muscle EMG as outlined above.

OBJECT OF THE INVENTION

It is an object of this invention to provide a method and apparatus for conducting electromyography of a deep muscle non-invasively.

SUMMARY OF THE INVENTION

In accordance with this invention there is provided a method of conducting electromyography of a deep muscle non-invasively comprising the application of an array of suitable surface electromyography electrodes to the skin of a patient and recording electrical potentials of selected electrodes relative to at least one other electrode, the method being characterised in that the array of electrodes is arranged in one or more rings encircling a part of the human body in which a deep muscle being investigated is located, recording the potential of at least selected electrodes relative to another electrode selected from a common reference electrode (mono-polar) and other electrodes (bi-polar) in the array; and processing the recorded potentials of at least some of said selected electrodes in order to determine (optionally using approximations or algorithms, or both) the contribution being made by at least said deep muscle being investigated.

Further features of the invention provide for the contributions to the potentials of the electrodes attributable to each of the encircled muscles including superficial muscles to be determined, typically mathematically by resolving the electromyography signals into their constituent components using independent component analysis (ICA) or any other suitable un-mixing or matrix inversion technique to result in the derivation of the electromyography waveforms of both deep and superficial muscles. The deep muscles may be indentified by selecting specific movement protocols that may be similar to those used to identify muscles by conventional (sEMG or needle/fine-wire) techniques.

Still further features of the invention provide for the results of a method as defined above to be integrated with those of a static muscle imaging device that may use the same electrodes to obtain a static tomogram of the muscles encircled; and for the static tomogram to be co-registered with the dipole decomposition or any other suitable 2D or 3D electrical source localisation technique of the ICA-sEMG waveforms. The static muscle imaging device may be an electrical impedance tomography device, an ultrasound device, computed tomography device (CT), or a magnetic resonance imaging device (MRI).

The invention also provides apparatus for carrying out a method as defined above, comprising multiple surface electromyography electrodes having flexible conductors connecting them individually to recording means and computing means adapted to carry out an independent component analysis, or any other suitable un-mixing or matrix inversion technique, on the potentials of the electrodes recorded in order to provide the electromyography waveform of at least one deep muscle encircled by one or more rings of multiple electrodes secured to the skin of the human body, in use.

Further features of the method and apparatus according to the invention will become more apparent from the following expanded description of the invention and its presently envisaged implementation, the description being made with reference to the accompanying drawings.

DETAILED DESCRIPTION WITH REFERENCE TO THE DRAWINGS

In one implementation of the invention the example of electromyography of the deep muscle brachialis (c) of the upper arm (2) as applied to an actual human subject in a laboratory setting, is given. In this implementation of the invention two arrays of suitable surface electromyography electrodes (3) are applied to the skin of a patient with the electrodes being arranged in two rings encircling the group of muscles in the appropriate part of the upper arm in which the relevant part of the brachialis is located.

Figure 3:
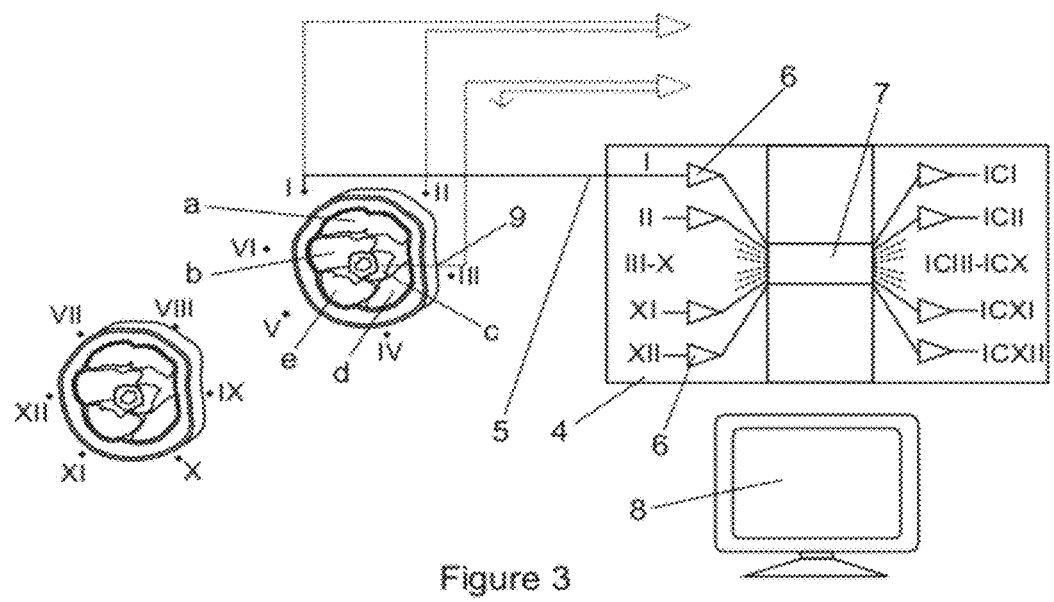
FIG. 3 is a schematic illustration of the operation of the invention in comparison to that of the prior art.

In this particular instance, the two arrays of electrodes comprise a total of 12 electrodes, with 6 electrodes per ring that are arranged generally equally spaced around the periphery of the arm. The electrodes, that are indicated in FIG. 3 by the Roman numerals (I, II, III, IV, V, VI, VII. VIII, IX, X, XI, XII) sequentially in a clockwise direction around the two rings, are connected to a processing unit (4) by means of flexible conductors (5) in the usual way.

Figure 1:
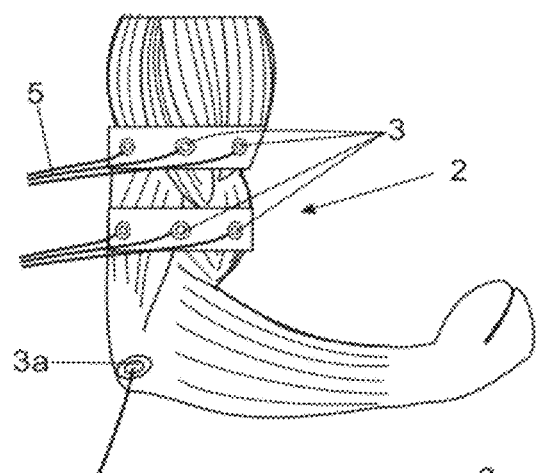
FIG. 1 is a schematic side illustration of a human arm illustrating the general positions of the various electrodes.

In so far as FIG. 3 is concerned only one pair of conductors is illustrated as being connected to the electrodes and processing unit, the relevant electrode being that indicated by Roman numeral I. A common reference electrode is also usually placed outside the ring, for example on the bony part of the elbow as indicated by numeral (3a) in FIG. 1, although it may sometimes be suitable to use one of the ring electrodes as the common reference. A ground electrode is placed on a suitable sEMG ground point (e.g. elbow, wrist, etc) for the muscles under investigation. This manner of illustration is employed for the purpose of simplifying the illustration.

The mono-polar potential of all electrodes relative to the common reference electrode, are fed to one of a corresponding set of differential amplifiers (6), the outputs of which are all fed to a computing device (7) such as a personal computer or a programmable micro-controller that is programmed to compute the independent component analysis (ICA) or any other suitable un-mixing or matrix inversion technique. This may be done using approximations or algorithms, or both, and typically along general lines for ICA described by Klemm, Matthias, Jens Haueisen, and Galina Ivanova. in an article entitled "Independent component analysis: comparison of algorithms for the investigation of surface electrical brain activity" in Medical & Biological Engineering & Computing 47, no. 4 (April 2009): 413-423 or any other suitable un-mixing or matrix inversion technique. Open-source software called 'EEGLAB' that implements some of the ICA algorithms can also be used as may be appropriate.

In this manner the recorded potentials of the electrodes are processed in order to determine the contribution made by at least said deep muscle that is under investigation and generally each of the muscles encircled by the array of electrodes. The computing device may also decompose the differential signals and perform other routine software functions such as archiving the data etc.

The apparatus typically includes a display device (8) such as a computer monitor that can display the corresponding electromyography waveforms.

The electromyography device of this invention may thus be used to contemporaneously derive an electromyograph corresponding to both superficial muscles indicated by letters (a, b, d, e) and the deep brachialis muscle (c).

It is to be noted that in conventional (non-invasive) surface electromyography of a superficial muscle such as that indicated by the letter (a) the potential between two adjacent electrodes indicated by Roman numerals (I) and (II) would be measured.

Prior art invasive needle electromyography of the deep muscle (c), on the other hand, is illustrated schematically by numeral (9) in which the potential of the deep muscle is measured relative to a surface reference electrode.

In exercising the present invention, however, the electrical activity of each muscle (a, b, c, d, e) may be measured simultaneously. These electrical activities may be represented as Ma, Mb, Mc, Md, and Me in which instance each mono-polar channel would include a weighted sum of components from each (superficial and deep) muscle source, ie.

$$sEMG(I)=AI.Ma+BI.Mb+CI.Mc+DI.Mc+EI.Md$$

$$sEMG(II)=AII.Ma+BII.Mb+CII.Mc+DII.Mc+EII.Md$$

$$sEMG(III)=AIII.Ma+BIII.Mb+CIII.Mc+DIII.Mc+EIII.Md$$

$$sEMG(IV)=AIV.Ma+BIV.Mb+CIV.Mc+DIV.Mc+EIV.Md$$

$$sEMG(V)=AV.Ma+BV.Mb+CV.Mc+DV.Mc+EV.Md$$

$$sEMG(VI)=AVI.Ma+BVI.Mb+CVI.Mc+DVI.Mc+EVI.Md$$

$$sEMG(VII)=AVII.Ma+BVII.Mb+CVII.Mc+DVII.Mc+EVII.Md$$

$$sEMG(VIII)=AVIII.Ma+BVIII.Mb+CVIII.Mc+DVIII.Mc+EVIII.Md$$

$$sEMG(IX)=AIX.Ma+BIX.Mb+CIX.Mc+DIX.Mc+EIX.Md$$

$$sEMG(X)=AX.Ma+BX.Mb+CX.Mc+DX.Mc+EX.Md$$

$$sEMG(XI)=AXI.Ma+BXI.Mb+CXI.Mc+DXI.Mc+EXI.Md$$

$$sEMG(XII)=AXII.Ma+BXII.Mb+CXII.Mc+DXII.Mc+EXII.Md$$

If each muscle activation were statistically independent (see discussions on independent component analysis (ICA) limitations below), then ICA may be applied to solve the system of 12 equations for the 5 unknowns. Note that similar ICA components (as measured by e.g. correlation) may be added together to form a single component such as may be done with the four biceps ICAs (ICI-ICIII, ICVI) in FIG. 8 and this process would ideally unmix the twelve equations such that:

$$ICA\text{-}sEMG(a)=Ma$$

$$ICA\text{-}sEMG(b)=Mb$$

$$ICA\text{-}sEMG(c)=Mc$$

$$ICA\text{-}sEMG(d)=Md$$

$$ICA\text{-}sEMG(e)=Me$$

The temporal variation of these ICA-sEMG waveforms with pre-determined movement protocols designed to differentiate the deep muscle under investigation from adjacent muscles, is sufficient to determine the identity of the muscle.

Figure 6:
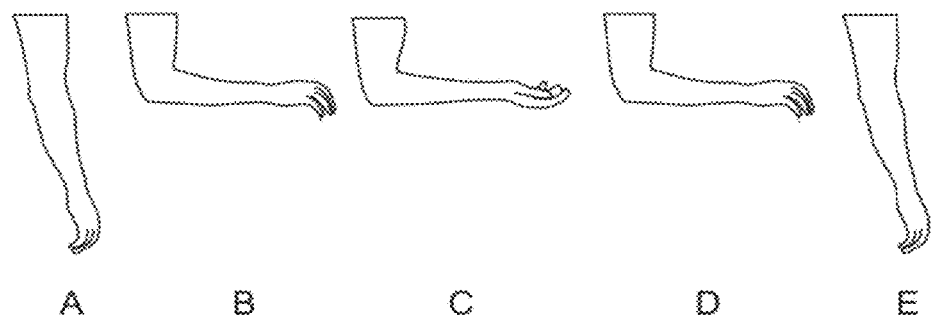
FIG. 6 is a representation of the five successive stages of the movement protocol used to isolate superficial (biceps) from deep (brachialis) muscle activity, for preliminary clinical results.

An example of this is provided using the movement protocol of FIG. 6 in which the sequence is illustrated commencing with the arm in an extended condition as indicated by (A); flexing it to a PRONATE position as indicated by (B); rotating the hand to a SUPINATE position as indicated by (C); returning to the PRONATE position as indicated by (D) and then extending the arm once more as indicated by (E). Each movement should take about 3 seconds and the movement from (A) to (B) activates the brachialis more than the biceps; the movement from (B) to (C) activates the biceps and reduces the brachialis; the movement from (C) to (D) activates the brachialis and reduces the biceps; and the movement from (D) to (E) activates the triceps.

Figure 2B:
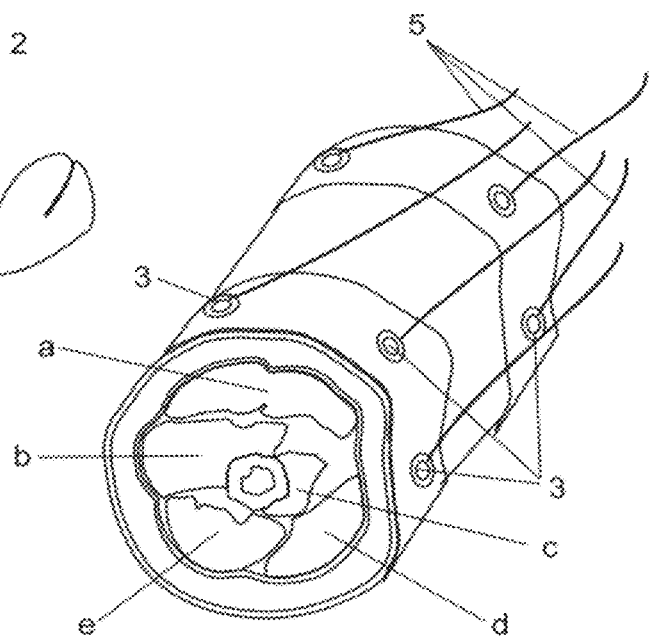
FIG. 2b is the same schematic section taken through the brachialis region of the arm and showing two spaced rings of electrodes encircling the arm.
Figure 2A:
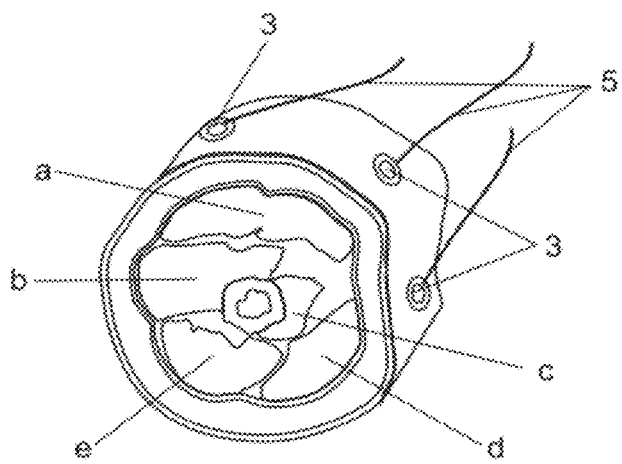
FIG. 2a is a schematic section taken through the brachialis region of the arm and showing a single ring of electrodes encircling the arm.
Figure 7:
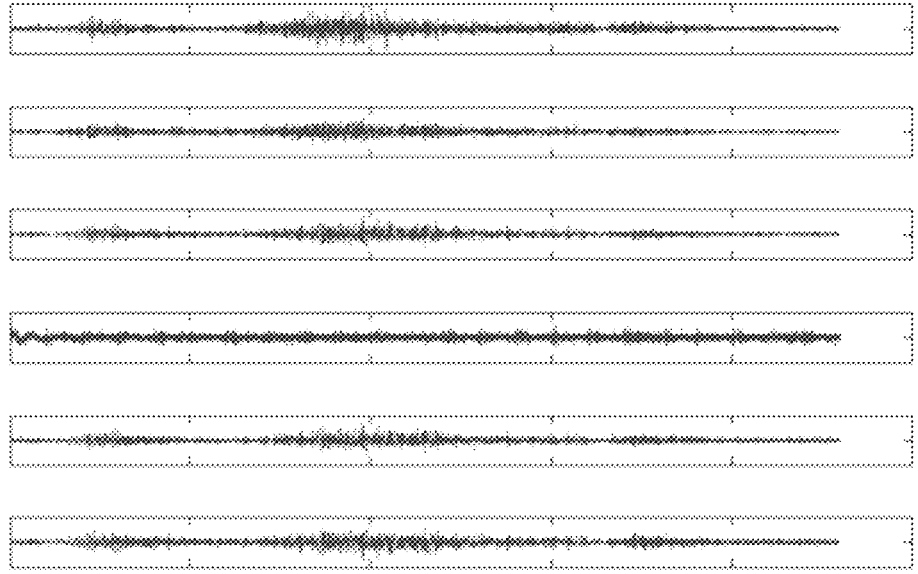
FIG. 7 illustrates un-processed mono-polar sEMG recordings from preliminary clinical results, using a 2 ring system with 6 electrodes per ring, following the movement protocol represented by FIG. 6 but with a 5 kg bar-bell.
Figure 7:
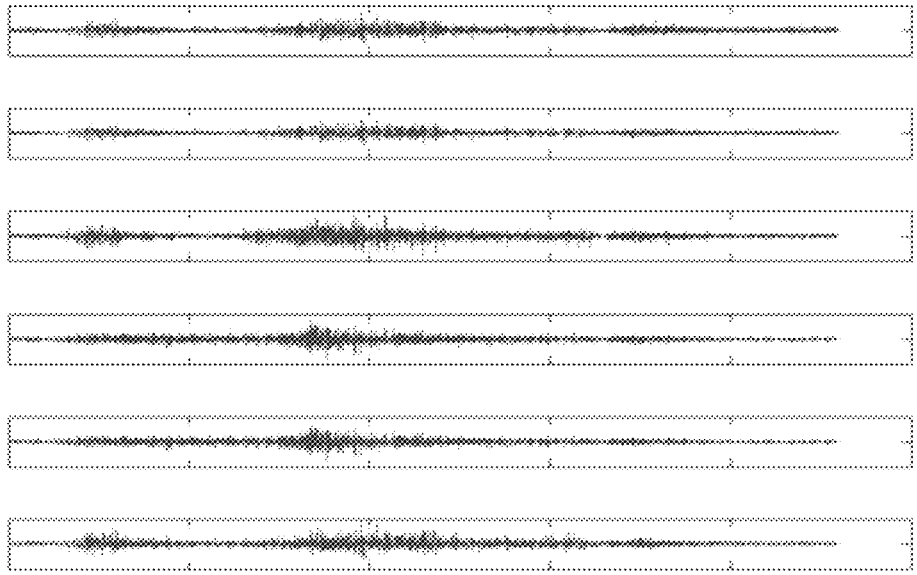

FIG. 7 illustrates the mono-polar sEMG (voltage in millivolts vs time in seconds) preliminary recordings from two rings positioned as illustrated in FIG. 2b in which each of the rings had six approximately equally spaced electrodes. The movement protocol was as described with reference to FIG. 6. It is to be noted that these mono-polar sEMG waveforms were dominated by biceps activity (most apparent during SUPINATE) and look similar to each other.

Figure 8:
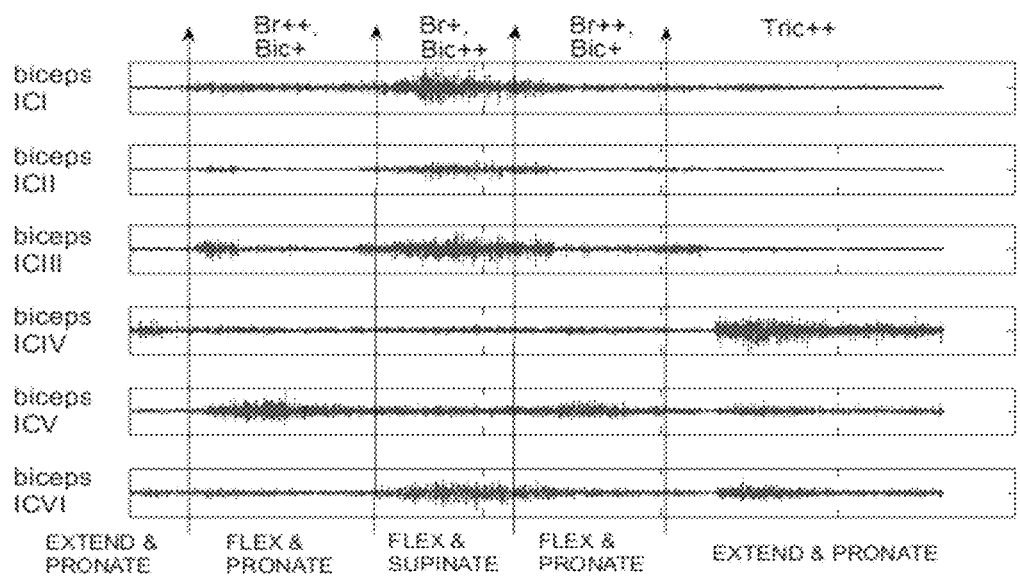
FIG. 8 illustrates the first six ICA-sEMG components derived from the sEMG recordings from FIG. 7, from preliminary clinical results; and, FIG. 9 illustrates the root mean square (RMS) values of the ICA-sEMG components of FIG. 8 during each of the five movement stages.

FIG. 8 illustrates the ICA transformation of the preliminary recordings shown in FIG. 7 and shows the first 6 ICA components (voltage in millivolts vs time in seconds). It is to be noted that the brachialis component activates on elbow flexion (FLEX) as well as on forearm pronation (PRONATE) and reduces on forearm supination (SUPINATE). The biceps consists of 4 components (ICI-ICIII, ICVI) that may be added together, all showing activation on flexion (FLEX), greater activation on forearm supination (SUPINATE) and reduced activation on forearm pronation (PRONATE). The triceps component shows activation on extension.

FIG. 8 thus illustrates that the difference between SUPINATE and PRONATE may be used to identify brachialis (ICV in FIG. 8) and biceps (ICI-ICIII, ICVI). Similarly the difference between the elbow flexed conditions (FLEX, SUPINATE, PRONATE) and the end EXTEND condition may be used to identify triceps (ICIV in FIG. 8).

Figure 4:
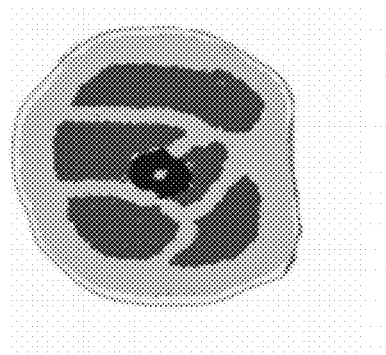
FIG. 4 is a representation of a static electrical impedance tomogram developed by the processing apparatus.
Figure 5:
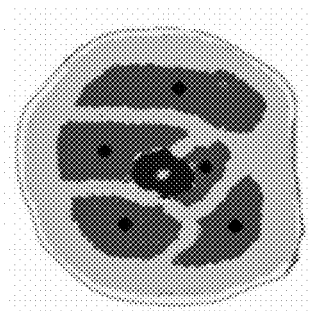
FIG. 5 is a representation of the electrical impedance tomogram (EIT) of the regions corresponding to the human arm cross-section of FIGS. 2 and 4 co-registered with computed dipoles.

If complementary muscle identifying information is required, a known static muscle imaging device such as muscle electrical impedance tomography (EIT) that uses the same electrodes as the sEMG ring, may then be applied to obtain a static tomogram of the muscles as illustrated in FIG. 4 and the static tomogram may be co-registered with the dipole decomposition or the electrical source localisation of the ICA-sEMG waveforms derived as described above (see FIG. 5) and as described further below.

The ICA-sEMG waveforms may be converted to their corresponding spatial locations (i.e. within the cross-sectional area of the circular electrode ring or rings) using electrical dipole analysis that, as far as applicant is aware, has not previously been applied to electromyography or standard electrical source localisation techniques including those implemented by Jesinger & Stonic (1994) or van den Doel (2008). This allows the muscle dipole or electrical source representing the ICA-sEMG to be tagged to a location in the cross-section. The dipole or electrical source cross-section may be co-registered with the muscle EIT to identify the location of the ICA-sEMG sources, hence also the identity of the deep muscle.

Figure 9:
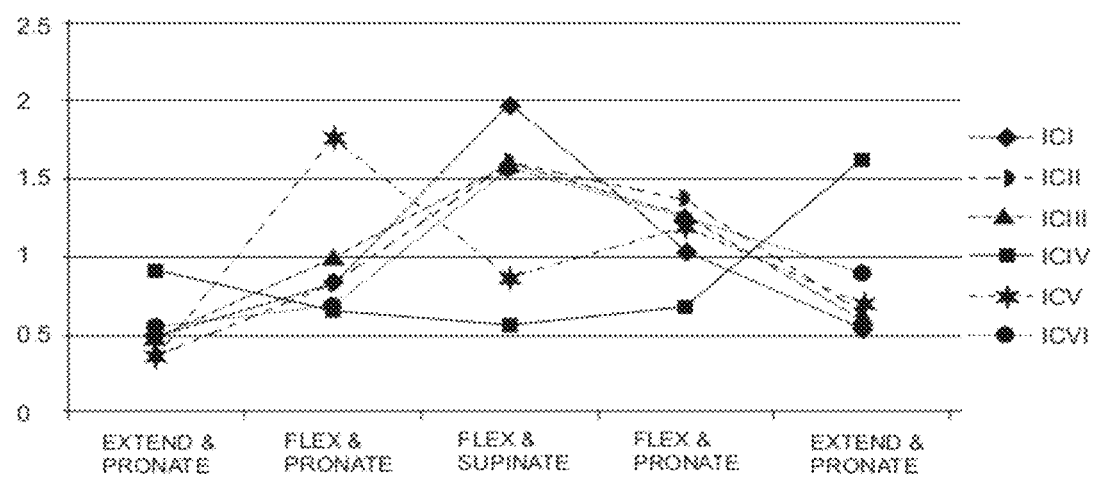

FIG. 9 illustrates the root mean square (RMS) values of the ICA-sEMG components during each of the five movement stages, from preliminary clinical results. These values share the same activation and reduction patterns with the biceps being represented by VI; the brachialis by ICV; and the triceps by ICIV.

It is to be noted that the apparatus described for developing the separate electromyographs may be a device on its own, where the ICA-sEMG may be related to specific muscles through pre-defined movement protocols i.e. a protocol that is known to activate a certain deep muscle would therefore also result in a corresponding ICA-sEMG waveform that mimics the activation of that muscle during that movement.

Also, if the apparatus is used in conjunction with an electronic imaging device, the EIT device as indicated above such imaging device could be replaced by another static imaging technology such as those identified above. At least some of those technologies may be expected to provide much more detailed images than EIT but may be cumbersome to use in environments requiring movement typical of functional muscular studies.

As with all new medical computing techniques the invention may become usable, or at least approved for use in specific areas where its accuracy has been verified.

It is also to be noted that ICA results in statistically independent channels whereas there is not necessarily a one-to-one relationship between an ICA-sEMG component and a specific muscle. An ICA-sEMG channel alone may not necessarily be sufficient to spatially localise a source (hence to identify the individual muscle), as its activity may be included in more than one ICA-sEMG component.

Options to overcome this potential limitation include combining ICA-sEMG components that are similar (such as described earlier) by using correlation or any other mathematically equivalent technique; the application of multiple dipole localization techniques such as have been applied to EEG to allow each ICA component to be spatially localized to a single or multiple source; two-dimensional or three-dimensional electrical source localisation techniques. Hence the EMG sourced from specific spatial locations (hence the specific muscles) may be reconstructed using a combination of ICA or any other suitable un-mixing or matrix inversion technique, multiple dipole source localization or any other electrical source technique, superimposed on, for example, a cross sectional tomogram of the region under investigation.

Numerous variations may be made to the method and apparatus described above without departing from the scope hereof. In particular, it is to be noted that the number of rings of electrodes can be varied with a minimum of one. Also, the potential of each electrode need not be measured relative to a reference electrode that the electrodes could be used in a bipolar system in which the potential of electrodes is measured relative to other active electrodes such as a diametrically opposite electrode. Numerous other variations may be made.

The invention claimed is:

1. A method of conducting electromyography of a deep muscle of a patient non-invasively comprising:
    applying an array of mono-polar surface electromyography electrodes to the skin of a patient at a location that includes the deep muscle and superficial muscles;
    recording electrical potentials of selected electrodes relative to at least one other electrode, the method being characterised in that the array of electrodes is arranged in one or more rings encircling a circumference of a part of the body of the patient in which the superficial muscles and the deep muscle being investigated are located;
    recording the potential of at least selected electrodes relative to another electrode selected from a common reference electrode and other electrodes in the array;
    processing the recorded potentials of at least some of said selected electrodes in order to determine, using approximations or algorithms, or both, a contribution being made by at least said deep muscle being investigated; and
    wherein the contributions to the potentials of the electrodes attributable to each of the muscles encircled by the array including the superficial muscles is determined mathematically by resolving the electromyography signals into constituent components using a technique selected from independent component analysis (ICA) and an unmixing or matrix inversion technique to result in a derivation of the electromyography waveforms of both the deep and the superficial muscles.

2. A method as claimed in claim 1 in which the deep muscles are identified by selecting specific movement protocols.

3. A method as claimed in claim 1 in which the determined contribution made by the deep muscle being investigated are integrated with results of a static muscle imaging device using the same electrodes to obtain a static tomogram of the superficial muscles encircled.

4. A method as claimed in claim 3 in which the static tomogram is co-registered with a dipole decomposition of the recorded potentials.

5. A method as claimed in claim 3 in which the static muscle imaging device is selected from an electrical impedance tomography device, an ultrasound device, a computed tomography device (CT), and a magnetic resonance imaging device (MRI).

6. Apparatus for carrying out a method as claimed in claim 1 comprising multiple surface electromyography electrodes having flexible conductors connecting them individually to a processing unit configured to carry out an independent component analysis or suitable un-mixing or matrix inversion technique on the potentials of the electrodes recorded in order to provide an electromyography waveform of at least one deep muscle encircled by one or more rings of multiple electrodes secured to the skin of the human body, in use.

7. A method of conducting non-invasive electromyography of a deep muscle of a patient, comprising the steps of:
    applying an array of mono-polar surface electromyography electrodes to the skin of the patient, wherein the array includes a plurality of surface electromyography electrodes arranged in one or more rings that encircle a circumference of a part of the human body in which both superficial muscles and the deep muscle being investigated are located;
    recording electrical potentials of selected electrodes relative to at least one other electrode selected from either a common reference electrode or another surface electromyography electrode in the array; and processing the recorded potentials of at least some of the selected electrodes using approximations or algorithms to determine a contribution made by at least the deep muscle being investigated.

* * * * *